US011219651B2

(12) United States Patent
Todo et al.

(10) Patent No.: US 11,219,651 B2
(45) Date of Patent: Jan. 11, 2022

(54) RECOMBINANT HERPES VIRUS AND PHARMACEUTICAL COMPOSITION CONTAINING THE SAME

(71) Applicant: The University of Tokyo, Tokyo (JP)

(72) Inventors: Tomoki Todo, Tokyo (JP); Hiroshi Fukuhara, Tokyo (JP)

(73) Assignee: The University of Tokyo, Tokyo (JP)

( * ) Notice: Subject to any disclaimer, the term of this patent is extended or adjusted under 35 U.S.C. 154(b) by 38 days.

(21) Appl. No.: 14/611,643

(22) Filed: Feb. 2, 2015

(65) Prior Publication Data
US 2015/0139954 A1 May 21, 2015

Related U.S. Application Data

(62) Division of application No. 13/579,628, filed as application No. PCT/JP2010/001078 on Feb. 19, 2010, now Pat. No. 8,945,531.

(51) Int. Cl.
| | |
|---|---|
| *A61K 39/245* | (2006.01) |
| *C12N 15/74* | (2006.01) |
| *C07H 21/04* | (2006.01) |
| *A61K 35/763* | (2015.01) |
| *C12N 15/86* | (2006.01) |
| *C12N 7/00* | (2006.01) |
| *A61K 35/76* | (2015.01) |
| *C12N 15/869* | (2006.01) |

(52) U.S. Cl.
CPC ............ *A61K 35/763* (2013.01); *A61K 35/76* (2013.01); *C12N 7/00* (2013.01); *C12N 15/86* (2013.01); *C12N 15/869* (2013.01); *C12N 2710/16621* (2013.01); *C12N 2710/16632* (2013.01); *C12N 2710/16643* (2013.01); *C12N 2710/16671* (2013.01); *C12N 2830/008* (2013.01)

(58) Field of Classification Search
CPC ................. C12N 15/86; C12N 15/869; C12N 2710/16632; A61K 35/763; C07H 21/04
See application file for complete search history.

(56) References Cited

U.S. PATENT DOCUMENTS

| | | | | |
|---|---|---|---|---|
| 5,728,379 A | * | 3/1998 | Martuza | A01K 67/0271 424/93.2 |
| 6,897,057 B1 | | 5/2005 | Chiocca et al. | |
| 7,223,593 B2 | * | 5/2007 | Coffin | A61K 35/763 424/93.2 |
| 2002/0187163 A1 | | 12/2002 | Johnson et al. | |
| 2004/0228841 A1 | | 11/2004 | Martuza et al. | |
| 2008/0132449 A1 | | 6/2008 | Yun et al. | |
| 2009/0215147 A1 | | 8/2009 | Zhang et al. | |

FOREIGN PATENT DOCUMENTS

| | | |
|---|---|---|
| JP | 2003-508055 A | 3/2003 |
| WO | WO 01/16331 A1 * | 3/2001 |

OTHER PUBLICATIONS

Carroll et al., 1996, Annals of Surgery, vol. 224, No. 3, p. 323-330.*
Mullen et al., 2002, Annals of Surgery, vol. 236, No. 4, p. 502-513.*
Sze et al., 1992, Virus Research, vol. 26, p. 141-152.*
Zhang et al., 2009, US 20090215147 A1.*
Aghi et al., 2008, Oncogene, vol. 27, p. 4249-4254.*
Chahlavi et al., "Effect of prior exposure to herpes simplex virus 1 on viral vector-mediated tumor therapy in immunocompetent mice," Gene Therapy, 6: 1751-1758 (1999).
Chahlavi et al., "Replication-Competent Herpes Simplex Virus Vector G207 and Cisplatin Combinational Therapy for Head and Neck Squamous Cell Carcinoma," Neoplasia, 1: 162-169 (1999).
Fukuhara et al., "Triple Gene-Delected Oncolytic Herpes Simplex Virus Vector Double-Armed with Interleukin 18 and Soluble B7-1 Constructed by Bacterial Artificial Chromosome-Mediated System," Cancer Research, 65: 10663-10668 (2005).
Jorgensen et al., "Ionizing Radiation Does Not Alter the Antitumor Activity of Herpes Simplex Virus Vector G207 in Subcutaneous Tumor Models of Human and Murine Prostate Cancer," Neoplasia, 3: 451-456 (2001).
Kanai et al., "Augmented Therapeutic Efficacy of an Oncolytic Herpes Simplex Virus Type 1 Mutant Expressing ICP34.5 Under the Transcriptional Control of musashil Promoter in the Treatment of Malignant Glioma," Human Gene Therapy, 18: 63-73 (2007).
Lee et al., "Novel Prostate-Specific Promoter Derived from PSA and PSMA Enhancers," Molecular Therapy, 6: 415-421 (2002).
Markert et al., "Conditionally replicating herpes simplex virus mutant, G207 for the treatment of malignant glioma: results of a phase I trial," Gene Therapy, 7: 867-874 (2000).
Martuza et al., "Experimental Therapy of Human Glioma by Means of a Genetically Engineered Virus Mutant," Science, 252: 854-856 (1991).
Matsubara et al., "A Conditional Replication-competent Adenoviral Vector, Ad-OC-E1a, to Cotarget Prostrate Cancer and Bone Stroma in an Experimental Model of Androgen-independent Prostrate Cancer Bone Metastasis," Cancer Research, 61: 6012-6019 (2001).
Nakamura et al., "Glial Expression of Fibroblast Growth Factor-9 in Rat Central Nervous System," GLIA, 28: 53-65 (1999).
Nakano et al., "Therapeutic Efficacy of G207, a Conditionally Replicating Herpes Simplex Virus Type 1 Mutant, for Gallbladder Carcinoma in Immunocompetent Hamsters," Molecular Therapy, 3: 431-437 (2001).
Todo et al., "Oncolytic Herpes Simplex Virus (G207) Therapy: From Basic to Clinical," Tumor-Suppressing Viruses, Genes, and Drugs Innovative Cancer Therapy Approaches, 45-75 (2001).

(Continued)

*Primary Examiner* — Shin Lin Chen
(74) *Attorney, Agent, or Firm* — Suzannah K. Sundby, Esq.; Canady + Lortz LLP

(57) ABSTRACT

A recombinant herpes virus showing high antitumor activity is provided. In particular, a recombinant herpes simplex virus that expresses an ICP6 gene under control of a tumor-specific promoter or tissue-specific promoter on the genome of the virus is provided.

16 Claims, 5 Drawing Sheets

Specification includes a Sequence Listing.

(56) References Cited

OTHER PUBLICATIONS

Todo et al., "Viral Shedding and Biodistribution of G207, a Multimutated, Conditionally Replicating Herpes Simplex Virus Type 1, after Intracerebral Inoculation in Aotus," Molecular Therapy, 2: 588-595 (2000).

Todo et al., "Systemic Antitumor Immunity in Experimental Brain Tumor Therapy Using a Multimutated, Replication-Competent Herpes Simplex Virus," Human Gene Therapy, 10: 2741-2755 (1999).

Todo et al., "Corticosteriod Administration Does Not Affect Viral Oncolytic Activity, but Inhibits Antitumor Immunity in Replication-Competent Herpes Simplex Virus Tumor Therapy," Human Gene Therapy, 10: 2869-2878.

Todo et al., "Evaluation of ganciclovir-mediated enhancement of the antitumoral effect in oncolytic, multimutated herpes simplex virus type 1 (G207) therapy of brain tumors," Cancer Gene Therapy, 7: 939-946 (2000).

Todo et al., "Oncolytic herpes simplex virus vector with enhanced MHC class I presentation and tumor cell killing," PNAS, 98: 6396-6401 (2001).

Varghese et al., "Preclinical Safety Evaluation of G207, a Replication-Competent Herpes Simplex Virus Type 1, Inoculated Intraprostatically in Mice and Nonhuman Primates," Human Gene Therapy, 12: 999-1010 (2001).

Hunter et al., "Attenuated, Replication-Competent Herpes Simplex Virus Type 1 Mutant G207: Safety Evaluation of Intracerebral Injection in Nonhuman Primates," Journal of Virology, 73: 6319-6326 (1999).

Chung et al., "B-myb Promoter Retargeting of Herpes Simplex Virus y34.5 Gene-Mediated Virulence toward Tumor and Cycling Cells," Journal of Virology, 73: 7556-7564 (1999).

Fukuhara et al., "Anticancer virus therapy successfully enhancing antitumor effects using cancer-specific hTERT promoter-kidney cancer cases," The Japanese Journal of Urology, 100: 106 (2009).

\* cited by examiner

DU145 PROSTATE CANCER CELLS

```
                             SEQUENCE LISTING

<160> NUMBER OF SEQ ID NOS: 10

<210> SEQ ID NO 1
<211> LENGTH: 23
<212> TYPE: DNA
<213> ORGANISM: Artificial
<220> FEATURE:
<223> OTHER INFORMATION: forward primer used for PCR amplification of
      ICP6-1 fragment

<400> SEQUENCE: 1
gtcgacgccg cgtctgttga aat                                              23

<210> SEQ ID NO 2
<211> LENGTH: 19
<212> TYPE: DNA
<213> ORGANISM: Artificial
<220> FEATURE:
<223> OTHER INFORMATION: reverse primer used for PCR amplification of
      ICP6-1 fragment

<400> SEQUENCE: 2
ctttccgtca ggccaaaat                                                   19

<210> SEQ ID NO 3
<211> LENGTH: 18
<212> TYPE: DNA
<213> ORGANISM: Artificial
<220> FEATURE:
<223> OTHER INFORMATION: forward primer used for PCR amplification of
      ICP6-2 fragment

<400> SEQUENCE: 3
catcctgggg gttctggt                                                    18

<210> SEQ ID NO 4
<211> LENGTH: 20
<212> TYPE: DNA
<213> ORGANISM: Artificial
<220> FEATURE:
<223> OTHER INFORMATION: reverse primer used for PCR amplification of
      ICP6-2 fragment

<400> SEQUENCE: 4
gcgtctttga acatgacgaa                                                  20

<210> SEQ ID NO 5
<211> LENGTH: 20
<212> TYPE: DNA
<213> ORGANISM: Artificial
<220> FEATURE:
<223> OTHER INFORMATION: forward primer used for PCR amplification of
      ICP6-3 fragment

<400> SEQUENCE: 5
gactttcacg gggaggagtt                                                  20

<210> SEQ ID NO 6
<211> LENGTH: 22
<212> TYPE: DNA
<213> ORGANISM: Artificial
<220> FEATURE:
<223> OTHER INFORMATION: reverse primer used for PCR amplification of
      ICP6-3 fragment
```

```
<400> SEQUENCE: 6
aggcctcaca gcgcgcagct ca                                              22

<210> SEQ ID NO 7
<211> LENGTH: 20
<212> TYPE: DNA
<213> ORGANISM: Artificial
<220> FEATURE:
<223> OTHER INFORMATION: forward primer used for PCR amplification of
      hTERT core promotor fragment

<400> SEQUENCE: 7
tcgggttacc ccacagccta                                                 20

<210> SEQ ID NO 8
<211> LENGTH: 19
<212> TYPE: DNA
<213> ORGANISM: Artificial
<220> FEATURE:
<223> OTHER INFORMATION: reverse primer used for PCR amplification of
      hTERT core promotor fragment

<400> SEQUENCE: 8
agggcttccc acgtgcgca                                                  19

<210> SEQ ID NO 9
<211> LENGTH: 20
<212> TYPE: DNA
<213> ORGANISM: Artificial
<220> FEATURE:
<223> OTHER INFORMATION: forward primer used for PCR amplification of OC
      promotor fragment

<400> SEQUENCE: 9
actagtgtcg acttgtctgt                                                 20

<210> SEQ ID NO 10
<211> LENGTH: 20
<212> TYPE: DNA
<213> ORGANISM: Artificial
<220> FEATURE:
<223> OTHER INFORMATION: reverse primer used for PCR amplification of OC
      promotor fragment

<400> SEQUENCE: 10
cttaagggta ccatctgtag                                                 20
```

RECOMBINANT HERPES VIRUS AND PHARMACEUTICAL COMPOSITION CONTAINING THE SAME

A computer readable text file, entitled "SequenceListing.txt," created on or about Aug. 16, 2012 with a file size of about 3 kb contains the sequence listing for this application and is hereby incorporated by reference in its entirety.

TECHNICAL FIELD

The present invention relates to a recombinant Herpes virus showing tumor-specific growth and a pharmaceutical composition containing the virus.

BACKGROUND ART

In recent years, attempts have been made to modify virus genomes by using genetic engineering techniques to make viruses which selectively replicate in cancer cells and apply these viruses to cancer treatment.

The concept of applying recombinant viruses to cancer treatment was advocated by Martuza et al. in 1991 (refer to, for example, Non-patent Document 1). Since many viruses are themselves pathogenic, direct administration to humans and so forth has detrimental effects on normal cells as well. However, by deleting or mutating specific genes by using genetic engineering, viruses can be made which are incapable of replicating in normal cells but are capable of replicating in actively growing tumor cells through mechanisms such as compensation of the deleted gene function.

Recombinant oncolytic viruses are genetically modified so as to selectively replicate only in cancer cells, replicate in situ upon infecting cancer cells and directly destroy host cancer cells during that process. Subsequently, the progeny viruses scatter around and infect cancer cells again. Then, they repeat replication, cell killing and infection and thus, produce anti-tumor effects. On the other hand, therapeutic viruses which have infected normal cells cannot replicate so that they do not cause damage to the normal tissue.

Examples of such mutant viruses which have been developed thus far include a mutant virus obtained by deleting the thymidine kinase (tk) gene from the genome of herpes simplex virus type 1 (HSV-1) (refer to, for example, the above-mentioned Non-patent Document 1); HSV-1 (which will hereinafter be called "G207") obtained by deleting both two copies of the γ34.5 gene and inactivating the ICP6 gene (refer to, for example, Non-patent Documents 2 to 14); and HSV-1 (which will hereinafter be called "G47Δ", refer to, for example, Patent Document 1 and Non-patent Document 15) obtained by deleting the ICP47 gene (also called α47 gene) in addition to deletion of both two copies of the γ34.5 gene and inactivation of the ICP6 gene. Although these mutant viruses are unable to replicate in normal cells, they retain the replication ability in tumor cells.

In particular, as a result of mutation of three genes, the G47Δ developed by the present inventors has high tumor specificity in virus replication and has high cytocidal effects limited to tumor cells, while it shows no toxicity in the normal tissue so that its safety is not damaged and antitumor effects are markedly improved compared with the parent G207 virus. In addition, the G47Δ permits production of a virus formulation having a higher titer compared with G207 so that G47Δ is expected to have a higher therapeutic effect when their volumes are equal.

FIG. 11 shows the structure of G47Δ. As shown in this figure, G47Δ has a 1-kb deletion in two γ34.5 genes and a 312-b depletion in the α47 gene and in addition, its ICP6 gene has been inactivated by inserting the lacZ-gene therein.

The γ34.5 gene is a gene related to pathogenicity of HSV-1 and a mutant obtained by deleting this gene has markedly reduced virus replication ability in normal cells. When virus infection occurs in normal cells, double-stranded RNA-activated protein kinase (PKR) is phosphorylated and the resulting protein kinase phosphorylates a translation initiation factor elF-2a, resulting in blocking of protein synthesis in cells containing a viral protein. Although the γ34.5 gene product antagonizes the phosphorylated PKR and permits synthesis of a viral protein, the γ34.5 gene-deficient HSV-1 cannot replicate in normal cells. It is however presumed that in tumor cells, the universally low phosphorylation level of PKR enables even the γ34.5 gene-deficient HSV-1 to replicate.

The ICP6 gene is a gene encoding the large subunit of ribonucleotide reductase (RR). RR is an enzyme necessary for virus DNA synthesis. Inactivation of this gene prevents virus replication in non-dividing cells. Only in cells which divide actively and have increased RR activity, the deficiency of the RR activity due to deletion of the ICP6 gene is compensated, enabling virus replication.

The α47 gene product inhibits the transporter associated with antigen presentation (TAP) in host cells to control expression of the MHC class I on the cell surface, thereby having an effect of suppressing presentation of a viral protein and escaping from immunosurveillance of the host. Accordingly, it is expected that in the α47-gene-deleted HSV-1, expression of the MHC class I of host cells is maintained and a stimulus to antitumor immune cells increases.

In addition, G47Δ also has a deletion of the promoter of the US11 gene which overlaps with the α47 gene so that the timing of US11 gene expression is accelerated. As a result, this gene functions as a second site suppressor of the γ34.5 gene mutation and it restores, only in tumor cells, the reduced virus replication ability in the γ34.5-deficient HSV-1.

As described above, G47Δ has four artificial mutations separated from each other on the virus genome so that there is almost no possibility of it reverting to wild type HSV-1. This suggests that G47Δ is a therapeutic virus having high tumor specificity and high safety and excellent in versatility and usefulness.

In G47Δ, however, the RR activity necessary for replication is compensated by the RR activity of tumor cells so that in theory, virus replication is not conducted efficiently in tumor cells not having sufficiently increased RR activity and there is a possibility of failing to obtain sufficient antitumor effects.

PRIOR ART DOCUMENTS

Patent Document

Patent Document 1: US2002/0187163A1

Non-Patent Documents

Non-patent Document 1: Martuza, R. L. et al.; Science 252: 854-6 (1991).
Non-patent Document 2: Chahlavi, A. et al.; Neoplasia 1: 162-169 (1999).
Non-patent Document 3: Hunter, W. D. et al.; J Virol 73: 6319-6326 (1999).

Non-patent Document 4: Chahlavi, A. et al.; Gene Ther 6: 1751-1758 (1999).
Non-patent Document 5: Nakamura, S. et al.; Glia 28: 53-65 (1999).
Non-patent Document 6: Todo, T et al.; Hum Gene Ther 10: 2741-2755 (1999).
Non-patent Document 7: Todo, T. et al.; Hum Gene Ther 10: 2869-2878 (1999).
Non-patent Document 8: Todo, T. et al.; Cancer Gene Ther. 7: 939-946 (2000).
Non-patent Document 9: Markert, J M. et al.; Gene Ther. 7: 867-874 (2000).
Non-patent Document 10: Todo, T. et al.; Mol. Ther. 2: 588-595 (2000).
Non-patent Document 11: Nakano, K. et al.; Mol. Ther. 3: 431-437 (2001).
Non-patent Document 12: Varghese, S. et al.; Hum. Gene Ther. 12: 999-1010 (2001).
Non-patent Document 13: Jorgensen, T J. et al.; Neoplasia 3: 451-456 (2001).
Non-patent Document 14: Todo, T. et al.: Tumor Suppressing Viruses, Genes and Drugs—Innovative Cancer Therapy Approaches, San Diego, Academic Press, 45-75 (2001).
Non-patent Document 15: Todo, T et al.; Proc. Natl. Acad. Sci. USA 98: 6396-6401 (2001)

SUMMARY OF THE INVENTION

Problem to be Solved by the Invention

An object of the present invention is therefore to provide a highly safe recombinant herpes virus showing high antitumor activity regardless of the kind, grade of malignancy, and growth ability of tumor cells.

Means for Solving the Problem

The present inventors have investigated, in various tumor cell lines, virus replication ability by using HSV-1 which has been inactivated only in the γ34.5 genes and α47 gene but is normal in the ICP6 gene and G47Δ which has been inactivated in these three genes. As a result, it has been found that in some of the tumor cell lines, the virus replication ability of the former one is significantly higher than that of G47Δ. It is presumed that in tumor cells in which a significant difference in the replication ability is observed, an increase in RR activity is not enough for compensating virus replication of G47Δ.

As a result of further investigation, it has also been found that by introducing, into the HSV-1 genome deficient in an endogenous ICP6 gene, an expression cassette capable of controlling expression of an ICP6 gene by using a tumor-specific promoter or tissue-specific promoter, it is possible to construct HSV-1 having high replication ability even in tumor cells with low RR activity and having no replication ability in normal cells, leading to the completion of the present invention.

Described specifically, the present invention relates to:

[1] a recombinant herpes simplex virus selectively replicating in tumor cells in which the endogenous ICP6 gene is deleted or inactivated and including, on the genome of the virus, an expression cassette constructed to express an ICP6 gene under control of a tumor-specific promoter or tissue-specific promoter;

[2] the recombinant herpes simplex virus as described above in [1], wherein the endogenous ICP6 gene has been inactivated by inserting the expression cassette in the endogenous ICP6 gene;

[3] the recombinant herpes simplex virus as described above in [1], wherein the expression cassette has been inserted into a deletion site of the endogenous ICP6 gene;

[4] the recombinant herpes simplex virus as described above in any one of [1] to [3], wherein the expression cassette has been inserted in a direction opposite to the endogenous ICP6 gene;

[5] the recombinant herpes simplex virus selectively replicating in cancer cells, having an endogenous ICP6 gene functionally linked to a tumor-specific promoter or tissue-specific promoter;

[6] the recombinant herpes simplex virus as described above in any one of [1] to [5], wherein the tumor-specific promoter or tissue-specific promoter is a promoter selected from the group consisting of a human telomerase reverse transcriptase (hTERT) promoter, a PSES promoter, and an osteocalcin (OC) promoter;

[7] the recombinant herpes simplex virus as described above in any one of [1] to [6], wherein a γ34.5 gene and/or an ICP47 gene is also deleted or inactivated;

[8] a pharmaceutical composition containing the recombinant herpes simplex virus as described above in any one of [1] to [7] as an active ingredient;

[9] the pharmaceutical composition as described above in [8], which is a therapeutic agent for a tumor;

[10] the pharmaceutical composition as described above in [9], wherein the tumor is selected from the group consisting of tumors with a low growth rate, benign tumors, and tumors with low ribonucleotide reductase activity;

[11] the pharmaceutical composition as described above in [9] or [10], wherein the tumor is a tumor selected from the group consisting of prostate cancer, kidney cancer, breast cancer, chondrosarcoma, and meningioma; and

[12] a method of treating a tumor, including administering a therapeutically effective amount of the recombinant herpes simplex virus as described above in any one of [1] to [7].

Effect of the Invention

The recombinant herpes virus of the present invention can express, in cells in which a tumor-specific promoter or tissue-specific promoter functions, an ICP6 gene without depending on the RR activity of infected cells so that it can produce a high antitumor effect not only in malignant tumors or tumors with a high growth rate but also in benign tumors or tumors with a low growth rate. In addition, the ICP6 gene is not expressed in cells in which a tumor-specific promoter or tissue specific promoter does not function so that the safety of the conventional ICP6-gene-inactivated herpes virus is maintained.

Figure 1:
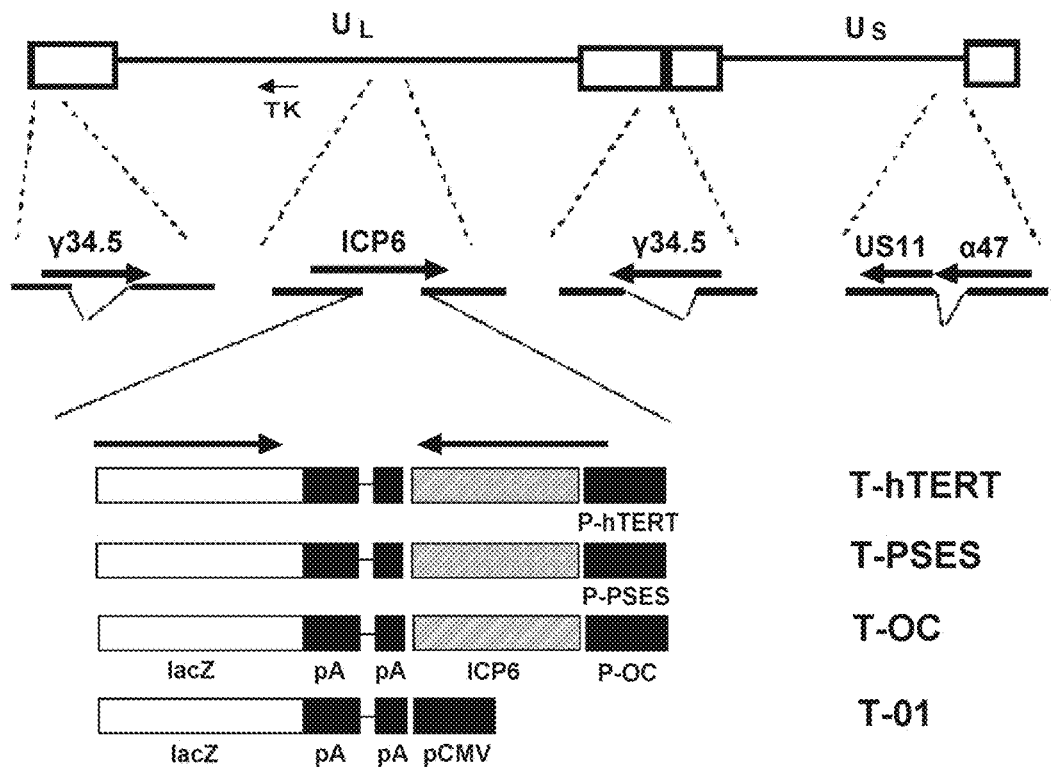
FIG. 1 is a schematic view showing the structures of the recombinant herpes viruses of the present invention (T-hTERT, T-PSES, and T-OC) and a T-01 virus used as a comparative example.

MODE FOR CARRYING OUT THE INVENTION (Recombinant Herpes Simplex Virus)

The recombinant herpes simplex virus in one aspect of the present invention is characterized by that the endogenous ICP6 gene has been deleted or inactivated and the virus has, on the genome thereof, an expression cassette constructed to express an ICP6 gene under control of a tumor-specific promoter or tissue-specific promoter.

The term "recombinant herpes simplex virus" as used herein means a herpes simplex virus (which may hereinafter be called "HSV") modified to produce the effect of the present invention by gene recombination technology. It may be obtained by modifying any of the genes of wild-type HSV or by inserting any of exogenous genes. The serum type of HSV may be either type 1 (HSV-1) or type 2 (HSV-2), preferably the type 1 (HSV-1).

The HSV-1 is classified as an enveloped, double-stranded DNA virus and it has the following characteristics advantageous in cancer treatment. 1) It is able to infect all types of human cells; 2) the virus life cycle and genome sequence have been elucidated; 3) the majority of the functions of the viral genes have been determined, and those genes can be genetically manipulated; and 4) large genes or multiple genes can be incorporated due to the large size of the virus genome (approx. 152 kb). Moreover, HSV-1 has the following advantages suitable for clinical application: 5) capable of destroying all cells at a relatively low multiplicity of infection (MOI); 6) there are anti-viral drugs capable of inhibiting growth; 7) anti-HSV-1 antibody in the blood does not affect the cell-to-cell spread of virus; 8) pre-clinical evaluations of safety and efficacy can be carried out in animals since there are mice and non-human primates sensitive to HSV-1; and 9) viral DNA stays outside the chromosomes without being incorporated into the genome of host cells.

The term "endogenous ICP6 gene" as used herein means a gene encoding infected cell protein 6 (ICP6) which HSV originally has on the genome thereof. ICP6 is the large subunit of ribonucleotide reductase (RR) and a key enzyme for nucleotide metabolism and viral DNA synthesis in non-dividing cells. When the ICP6 gene is deleted or inactivated, HSV cannot replicate in normal non-dividing cells. In actively dividing cells with increased RR activity, however, the deficient enzyme activity of the virus is compensated, enabling the virus to replicate.

The term "deletion or inactivation of a gene" means deletion of the whole or portion of the gene or suppression of expression of the gene through substitution of some bases, modification, insertion of an unnecessary sequence or the like.

The deletion or inactivation of the endogenous ICP6 gene can be conducted by those skilled in the art in a known method or a method based thereon. For example, a method using homologous recombination can be employed. For example, it is possible to divide and inactivate the ICP6 gene by cloning a DNA fragment containing a portion of the ICP6 gene and a sequence unrelated to the ICP6 gene in a suitable plasmid vector and then introducing it into HSV to cause homologous recombination in some region of the ICP6 gene. As an alternative, it is also possible to delete the ICP6 gene by constructing a DNA fragment containing the upstream and downstream of the ICP6 gene and not containing the ICP6 gene to cause homologous recombination.

The term "tumor-specific promoter or tissue-specific promoter" as used herein means a promoter permitting expression of a gene, which is under control of the promoter, specifically in a desired tumor cell or tissue.

Examples of the tissue-specific promoters that can be used in the invention include a prostate-specific antigen (PSA) promoter, which is specific for cells of the prostate; a prostate-specific membrane antigen (PSMA) promoter; the PSES promoter specific for cells of the prostate (Lee S J et al., Mol Ther., 6(3):415-421, 2002); the osteocalcin (OC) promoter (Matsubara S. et al., Cancer Res., 61(16):6012-6019, 2001); a HER2/neu promoter; a PEPCK promoter; a casein promoter; an IgG promoter; a chorionic embryonic antigen promoter; an elastase promoter; a porphobilinogen deaminase promoter; an insulin promoter; a growth hormone factor promoter; an acetylcholine receptor promoter; an alcohol dehydrogenase promoter; an α or β globin promoter; a T-cell receptor promoter; an IL-2 promoter; an IL-2 receptor promoter; a whey (wap) promoter and MHC class II promoter; the desmin promoter, which is specific for muscle cells (Li et al., Gene 78:243, 1989; Li et al., J. Biol. Chem. 266:6562, 1991; Li et al., J. Biol. Chem. 268:10403, 1993); the enolase promoter, which is specific for neurons (Forss-Petter et al., J. Neuroscience Res. 16(1):141-156, 1986); the β-globin promoter, which is specific for erythrocytes (Townes et al., EMBO J. 4:1715, 1985); the τ-globin promoter (tau-globin), which is also specific for erythrocytes (Brinster et al., Nature 283:499, 1980); the growth hormone promoter, which is specific for pituitary cells (Behringer et al., Genes Dev. 2:453, 1988); the insulin promoter, which is specific for pancreatic a cells (Selden et al., Nature 321:545, 1986); the glial fibrillary acidic protein promoter, which is specific for astrocytes (Brenner et al., J. Neurosci. 14:1030, 1994); the tyrosine hydroxylase promoter, which is specific for catecholaminergic neurons (Kim et al., J. Biol. Chem. 268:15689, 1993); the amyloid precursor protein promoter, which is specific for neurons (Salbaum et al., EMBO J. 7:2807, 1988); the dopamine β-hydroxylase promoter, which is specific for noradrenergic neurons and adrenergic neurons (Hoyle et al., J. Neurosci. 14:2455, 1994); the tryptophan hydroxylase promoter, which is specific for serotonin/pineal gland cells (Boularand et al., J. Biol. Chem. 270:3757, 1995); the choline acetyltransferase promoter, which is specific for cholinergic neurons (Hersh et al., J. Neurochem. 61:306, 1993); the aromatic L-amino acid decarboxylase (AADC) promoter, which is specific for catecholaminergic/5-HT/D-type cells (Thai et al., Mol. Brain Res. 17:227, 1993); the proenkephalin promoter, which is specific for neuronal/spermatogenic epididymal cells (Borsook et al., Mol. Endocrinol. 6:1502, 1992); the reg (pancreatic stone protein) promoter, which is specific for colon and rectal tumors, and pancreas and kidney cells (Watanabe et al., J. Biol. Chem. 265:7432, 1990); the parathyroid hormone-related peptide (PTHrP) promoter, which is specific for liver and cecum tumors, and neurilemoma, kidney, pancreas, and adrenal cells (Campos et al., Mol. Rnfovtinol. 6:1642, 1992); the albumin promoter, which is specific for hepatocytes (Huber, Proc. Natl. Acad. Sci. U.S.A. 88:8099, 1991); and the calponin promoter, which is specific for smooth muscle cells (Yamamura et al., Cancer Res. 61:3969, 2001).

Examples of the tumor-specific promoters to be used in the present invention include the telomerase reverse transcriptase promoter (hTERT promoter) (Komata et al., Cancer Res. 61, 2001:5796-5802); the glial fibrillary acidic protein promoter (GFAP promoter), which is specific for astrocytes or glioma cells (Vandier et al., Cancer Gene Ther. 7, 2000:1120-1126, etc.); an E2F promoter; a survivin promoter, a COX-2 promoter, an EGD-2 promoter; an ELF-1 promoter; a hypoxia-specific promoter; a carcinoembryonic antigen (CEA) promoter; the stromelysin 3 promoter, which is specific for breast cancer cells (Basset et al., Nature 348:699, 1990); the surfactant protein A promoter, which is specific for non-small cell lung cancer cells (Smith et al., Hum. Gene Ther. 5:29-35, 1994); the secretory leukoprotease inhibitor (SLPI) promoter, which is specific for SLPI-expressing carcinomas (Garver et al., Gene Ther. 1:46-50, 1994); the tyrosinase promoter, which is specific for melanoma cells (Vile et al., Gene Therapy 1:307, 1994; WO 94/16557; WO 94/004196); the stress inducible grp78/BiP promoter, which is specific for fibrosarcoma/tumorigenic cells (Gazit et al., Cancer Res. 55(8):1660, 1995); the AP2 adipose enhancer, which is specific for adipocytes (Graves, J. Cell. Biochem. 49:219, 1992); the α-1 antitrypsin transthyretin promoter, which is specific for hepatocytes (Grayson et al., Science 239:786, 1988); the interleukin-10 promoter, which is specific for glioblastoma multiform cells (Nitta et al., Brain Res. 649:122, 1994); the c-erbB-2 promoter, which is specific for pancreatic, breast, gastric, ovarian, and non-small cell lung cancer cells (Harris et al., Gene Ther. 1:170, 1994); the α-B-crystallin/heat shock protein 27 promoter, which is specific for brain tumor cells (Aoyama et al., Int. J. Cancer 55:760, 1993); the basic fibroblast growth factor promoter, which is specific for glioma and meningioma cells (Shibata et al., Growth Fact. 4:277, 1991); the epidermal growth factor receptor promoter, which is specific for squamous cell carcinoma, glioma, and breast tumor cells (Ishii et al., Proc. Natl. Acad. Sci. U.S.A. 90:282, 1993); the mucin-like glycoprotein (DF3, MUC1) promoter, which is specific for breast cancer cells (Abe et al., Proc. Natl. Acad. Sci. U.S.A. 90:282, 1993); the mts1 promoter, which is specific for metastatic tumors (Tulchinsky et al., Proc. Natl. Acad. Sci. U.S.A. 89:9146, 1992); the NSE promoter, which is specific for small-cell lung cancer cells (Forss-Petter et al., Neuron 5:187, 1990); the somatostatin receptor promoter, which is specific for small cell lung cancer cells (Bombardieri et al., Eur. J. Cancer 31A:184, 1995; Koh et al., Int. J. Cancer 60:843, 1995); the c-erbB-3 and c-erbB-2 promoters, which are specific for breast cancer cells (Quin et al., Histopathology 25:247, 1994); the c-erbB4 promoter, which is specific for breast and gastric cancer cells (Rajkumar et al., Breast Cancer Res. Trends 29:3, 1994); the thyroglobulin promoter, which is specific for thyroid cancer cells (Mariotti et al., J. Clin. Endocrinol. Meth. 80:468, 1995); the α-fetoprotein promoter, which is specific for hepatoma cells (Zuibel et al., J. Cell. Phys. 162:36, 1995); the villin promoter, which is specific for gastric cancer cells (Osborn et al., Virchows Arch. A. Pathol. Anat. Histopathol. 413:303, 1988); a calponin promoter, which is specific for sarcoma; and an albumin promoter, which is specific for hepatoma cells.

The tumor-specific promoters are preferred because they have versatility. Among them, the hTERT promoter and E2F promoter are particularly preferred. As shown later in Examples, the present inventors have confirmed that a virus (T-hTERT) using an hTERT promoter as a tumor-specific promoter is effective against slow growth cancers.

Of the above-exemplified tumor-specific promoters and tissue-specific promoters, a human telomerase reverse transcriptase (hTERT) promoter, a PSES promoter, an osteocalcin (OC) promoter, and an E2F promoter are particularly preferred.

The term "expression cassette constructed to express an ICP6 gene under control of a tumor-specific promoter or tissue-specific promoter" means a DNA construct in which an ICP6 gene has been operably linked downstream of a tumor-specific promoter or tissue-specific promoter.

The expression cassette may contain, in addition to the ICP6 gene and promoter, a terminator sequence for terminating transcription, a regulatory element such as enhancer, a selection marker (for example, lacZ gene, neomycin resistance gene, puromycin resistance gene, dihydrofolic acid reductase gene, or ampicillin resistance gene), a splicing signal, a poly-A-addition signal, and a ribosome binding sequence (S-D sequence).

In the recombinant HSV according to the present invention, the expression cassette may be inserted into any position on the genome insofar as it functions. For example, the expression cassette is inserted preferably in the endogenous ICP6 gene. In such a constitution, the endogenous ICP6 gene can be inactivated simultaneously with insertion of the expression cassette.

Alternatively, after deletion of the whole or part of the endogenous ICP6 gene, the expression cassette may be inserted into the deletion site. In such a constitution, natural recombination can be prevented and more stable recombinant HSV-1 can be constructed.

The expression cassette is inserted preferably in a direction opposite to the original direction of the ICP6 gene. The term "inserted in a direction opposite to the original direction" means that the 5'-terminal→3'-terminal direction of the expression cassette is opposite to the original 5'-terminal→3'-terminal direction of the ICP6 gene. Such a constitution makes it possible to prevent expression of the thus-inserted ICP6 gene, which will otherwise occur by the influence of the endogenous ICP6 promoter, thereby preventing growth of HSV in normal cells.

Since the herpes simplex virus according to the first aspect of the present invention has the above-mentioned constitution, the promoter of the expression cassette does not function in normal non-dividing cells and the ICP6 gene is not expressed. As a result, the virus cannot replicate. On the other hand, in actively dividing cells with increased RR activity, the virus can replicate because its missing enzyme is compensated. In the cells in which the tumor-specific promoter or tissue-specific promoter functions, an endogenous ICP6 gene is expressed, enabling the virus to replicate.

The recombinant herpes simplex virus in a second aspect of the present invention is characterized by that the endogenous ICP6 gene has been functionally linked to a tumor-specific promoter or tissue-specific promoter. This recombinant herpes simplex virus cannot also replicate because the promoter does not function in normal non-dividing cells and the ICP6 gene is not expressed. In actively dividing cells with increased RR activity, on the other hand, their missing enzyme is compensated, enabling the virus to replicate. In the cells in which the tumor-specific promoter or tissue-specific promoter functions, the endogenous ICP6 gene is expressed, enabling the virus to replicate.

The term "gene has been functionally linked to a promoter" as used herein means that the gene has been operably linked downstream of the promoter and in this constitution, the gene is expressed under control of the promoter.

The endogenous ICP6 gene and the tumor-specific promoter or tissue-specific promoter can be linked functionally by the known method or a method based thereon. For example, a method using homologous recombination can be employed. Described specifically, a DNA fragment containing the upstream and downstream of the promoter of the endogenous ICP6 gene and at the same time containing a tumor-specific promoter or tissue-specific promoter instead of the endogenous promoter is introduced into HSV after cloning it in an appropriate plasmid vector. As a result, homologous recombination occurs in the promoter region of the ICP6 gene and the endogenous promoter is substituted with the tumor-specific promoter or tissue-specific promoter.

The tumor-specific promoter and the tissue-specific promoter to be used in the second aspect of the recombinant herpes simplex virus of the present invention are similar to those used in the first aspect.

The recombinant HSV of the present invention may preferably contain another mutation in order to prevent reversion to a wild type and enhance its safety. Examples of such a mutation include deletion or inactivation of the endogenous γ34.5 gene, ICP47 gene, α0 gene (ICP0 gene), $U_L41$ gene (vhs gene) or $U_L56$ gene.

The γ34.5 gene is a gene related to pathogenicity of HSV-1 and it is known that a mutant strain lacking this gene has markedly reduced virus replication ability in normal cells. In normal cells, a double-stranded RNA-activated protein kinase (PKR) is phosphorylated in response to HSV-1 infection. The phosphorylated PKR phosphorylates a translation initiation factor eIF-2a, resulting in blocking of protein synthesis in cells containing a viral protein. Since the γ34.5 gene product antagonizes the function of the phosphorylated PKR, functioning of the γ34.5 gene may lead to synthesis of a viral protein in normal cells. When the γ34.5 gene does not function, on the other hand, virus replication is prevented in normal cells. Since the phosphorylation of PKR is suppressed universally in tumor cells, however, even in a γ34.5 gene-deficient or -inactivated mutant, virus replication can be achieved.

Deletion or inactivation of the γ34.5 gene, similar to deletion or inactivation of the ICP6 gene, can be carried out in a known manner by those skilled in the art. It is preferred to delete both two copies of the γ34.5 gene.

The ICP47 gene product inhibits a transporter associated with antigen presentation (TAP) to reduce expression of MHC class I of the infected cell, thereby enabling the virus to escape from immunosurveillance of the host. When the ICP47 gene is deleted or inactivated, expression of the MHC Class I of the infected tumor cell is maintained, leading to antitumor immunoenhancement. Accordingly, administration of ICP47-gene-deficient or -inactivated HSV induces systemic immune response of patients so that it is also useful for the treatment or prevention of metastatic cancer.

The deletion or inactivation of the ICP47 gene, similar to the deletion or inactivation of the ICP6 gene, can be carried out in a known manner by those skilled in the art.

The ICP47 gene can be inactivated, for example, by mutating the BstEII-EcoN1 fragment of the BamHIxfragment of HSV. It is particularly preferred to delete all or part of the BstEII-EcoN1 fragment. According to this method, the promoter of the $U_S11$ gene overlapping with the α47 gene is deleted, which makes the expression of the $U_S11$ gene earlier. The $U_S11$ gene, when expressed early, functions as a second site suppressor of the γ34.5 gene so that it is effective for recovering the reduced virus replication ability caused by deletion or inactivation of the γ34.5 gene, only in tumor cells.

As an inactivation method of the ICP47 gene, it is also preferred to fuse the ICP47 gene with DNA encoding a peptide suppressing the expression of the ICP47 gene. Examples of such a peptide include PEST sequences which are rich in proline, glutamate, serine, or threonine, and thus provide intramolecular signals for rapid proteolytic degradation (Rechsteiner et al., Trends Biochem. Sci. 21(7):267-271, 1996).

When inactivation of the ICP47 does not cause early expression of the $U_S11$ gene, it is preferred that the recombinant HSV according to the present invention further contains, upstream of the $U_S11$ gene, a promoter causing early expression of the $U_S11$ gene. Examples of such a promoter include a human cytomegalovirus (CMV) IE promoter, an HSV-1 IE promoter, an HSV-1 E promoter, and any other heterologous promoter that is active before the onset of DNA replication in the HSV genome.

The recombinant HSV according to the present invention can be constructed by adding the above-mentioned mutation to the HSV genome.

The HSV containing a deletion or inactivation of the γ34.5 gene, ICP6 gene, and/or ICP47 gene is, as described above, G207 obtained by deleting both two copies of the γ34.5 gene and inactivating the ICP6 gene and G47Δ obtained by deleting two copies of the γ34.5 gene, inactivating the ICP6 gene, and deleting the ICP47 gene, or the like. Thus, the recombinant HSV of the present invention can also be constructed by adding further alterations to G207 or G47Δ.

As described above, the recombinant HSV according to the present invention cannot replicate in normal cells but can replicate only in tumor cells with high RR activity or cells in which a tumor-specific promoter or tissue-specific promoter controlling the expression of an ICP6 gene can function so that it has high safety. In addition, it can grow regardless of the RR activity in cells in which a tumor-specific promoter or tissue-specific promoter can function so that it exhibits cytocidal effects even in cancers showing low RR activity and relatively slow growth or benign tumors.

(Pharmaceutical Composition)

The present invention also includes a pharmaceutical composition containing the above-mentioned recombinant HSV of the present invention. The pharmaceutical composition according to the present invention grows specifically in tumor cells and exhibits cytocidal effects even in cancers showing low RR activity and relatively slow growth or in benign tumors, suggesting that it is also effective against tumors against which conventional recombinant HSV has not produced sufficient therapeutic effects.

The pharmaceutical composition of the present invention produces cytocidal effects in cells in which a tissue-specific promoter or tumor-specific promoter capable of specifically expressing an ICP6 gene functions. The pharmaceutical composition of the present invention is therefore effective against any disease that can be treated by destroying cells in which a tissue-specific promoter or tumor specific promoter functions.

Examples of the disease against which the pharmaceutical composition of the present invention is effective include nervous-system type tumors, for example, astrocytoma, oligodendroglioma, meningioma, neurofibroma, glioblastoma, ependymoma, Schwannoma, neurofibrosarcoma, neuroblastoma, pituitary tumor (e.g., pituitary adenoma), and medulloblastoma, melanoma, brain tumor, prostate cancer, head and neck cancer, esophagus cancer, kidney cancer, renal cell cancer, pancreatic cancer, breast cancer, lung cancer, colon cancer, bowel cancer, gastric cancer, skin cancer, ovary cancer, bladder cancer, fibrosarcoma, squamous cell carcinoma, neurectodermal, thyroid tumor, lymphoma, hepatoma, mesothelioma, epidermoid carcinoma, and benign tumors (for example, benign tumors of the thyroid and benign prostatic hypertrophy).

Since the pharmaceutical composition of the present invention is, as described above, highly effective even in tumor cells with low RR activity, it is particularly useful in kidney cancer, prostate cancer, breast cancer, and chondrosarcoma that grow slowly and in benign tumors such as meningioma. On the other hand, the pharmaceutical composition of the present invention shows, in tumor cells with high RR activity, cytocidal effects equal to those of the conventional recombinant HSV depending on the RR activity of the tumor cells so that it is also useful in these tumors.

No particular limitation is imposed on the administration method of the pharmaceutical composition of the present invention. It can be administered, for example, intravenously, intra-arterially, intraventricularly, intraperitoneally, intrathoracically, intrathecally, subcutaneously, intracutaneously, intraepidermally, intramuscularly, or mucocutaneously (for example, intraocularly, intranasally, intrapulmonarily, buccally, intestinally, intrarectally, intravaginally, or within the surface of the urinary tract). It is preferably administered directly to the tumor tissue through injection, an endoscope, or surgical means.

The pharmaceutical composition of the present invention can be formulated by any formulation method for introducing a virus into the body of mammary animals including human beings. For example, the pharmaceutical composition of the present invention may contain an adjuvant or a desired carrier. Alternatively, it may only be diluted with a physiologically acceptable solution such as sterile physiological saline or sterile buffered physiological saline without adding an adjuvant or carrier.

The pharmaceutical composition of the present invention contains a therapeutically effective amount of the recombinant HSV of the present invention. The term "therapeutically effective amount" as used herein means an amount of an acting substance to alleviate, to some extent, one or more symptoms of the disease to be treated by the composition. When the pharmaceutical composition is an antitumor agent, the term "therapeutically effective amount" means an amount causing at least one of reduction in the tumor size, inhibition (retardation or termination) of the transfer of a tumor, inhibition (retardation or termination) of growth of a tumor, and alleviation of one or more symptoms related to cancer. The specific amount may be determined as needed by those skilled in the art, based on the seriousness of the symptom, age, sex, weight, or sensitivity of the subject to be treated, administration method, administration timing, administration interval, property of the formulation, intensity of the promoter, or the like.

The pharmaceutical composition of the present invention may be administered in an amount of from about $10^1$ to about $10^{12}$ plaque forming units (pfu), preferably from about $10^7$ to about $10^{10}$ pfu, more preferably from about $10^8$ to about $5 \times 10^9$ pfu, through injection once or in several portions.

Furthermore, the pharmaceutical composition of the present invention may contain another effective component or may be used in combination with a pharmaceutical composition containing another effective component.

It is to be understood that the terminology used herein is used for the purpose of describing particular embodiments and is not intended to limit the scope of the present invention.

The term "comprising", "containing", or "including" as used herein intends that the described respects (members, steps, elements and numerals, etc.) are present except it should be understand quite differently in context, and it is not excluded that the respects (members, steps, elements and numerals, etc.) other than these are present.

Unless otherwise defined differently, all of the terms (including technical terms and scientific terms) used herein have the same meanings as those understood widely by those skilled in the art to which the present invention belongs. The terms used herein should be construed to have the meanings coherent to the meanings in this specification and the related technical field unless a different definition is otherwise manifested, and should not be construed in idealized or unduly formal meanings.

The embodiments of the present invention are sometimes described with reference to the schematic view. When described in the schematic view, the embodiment is sometimes expressed in an exaggerated manner in order to describe it clearly.

EXAMPLES

The following examples and tests are shown only for illustrative purposes and the present invention is not limited to the specific examples indicated below. Those skilled in the art are able to maximally perform the present invention by adding various modifications to the following examples, and those modifications are embraced in the scope of the claims of the present application.

With regard to the cells used in the following tests, Vero cells (African green monkey kidney), U87MG cells, and OSRC2 cells were obtained from ATCC and cultured in a DMEM medium (Collegro) containing 10% FCS, while DU145 cells were obtained from ATCC and cultured in an MEM medium containing 10% FBS, 1% non-essential amino acid, and 1% sodium pyruvate.

1. Construction of Recombinant HSV-1

As the recombinant HSV of the present invention, constructed were recombinant HSV-1s (which are called "T-hTERT", "T-PSES", and "T-OC") having an ICP6 gene regulated by a tumor-specific human telomerase reverse transcriptase promoter (hTERT promoter), a prostate-specific PSES promoter, and osteocalcin promoter (OC promoter), respectively. As a control, T-01 having a partial deletion of the ICP6 gene and having, in the γ34.5 gene and α47 gene, the same mutation as that of G47Δ was used.

The schematic view of the genome of each virus is shown in FIG. 1. The boxes on the line in the upper panel show terminal or inverted long and short repeat sequences adjacent to long and short unique sequences ($U_L$ and $U_S$, respectively) of HSV-1 DNA. As shown in this figure, each of these viruses has a 1.0-kb deletion in each of the two γ34.5 genes, a 312-bp deletion in the α47 gene, and an 894-bp deletion in the ICP6 gene. An expression cassette containing the ICP6 gene controlled by each promoter has been inserted in the endogenous ICP6 gene so that the direction of the ICP6 gene is opposite to that of the endogenous ICP6 gene. The lacZ gene has been inserted into the expression cassette as a marker. A thick arrow shows a transcribed region.

These viruses were constructed using the process (T-BAC system; Fukuhara et al., Cacner Res 65:10663-10668, 2005) of constructing a recombinant HSV-1 for viral therapy using the bacteria artificial chromosome developed by the present inventors and two recombinase system (Cre/loxP and Flp/FRT). Described specifically, a shuttle vector containing each of the cassettes shown in FIG. 1 was constructed. The resulting vector was inserted into the loxP site of T-BAC by using Cre recombinase. The construct thus obtained and an FLP expression plasmid were cotransfected in Vero cells (African green monkey kidney), followed by excision of the site between the two FRT sites from T-BAC. Viruses were grown and the clone was isolated by limiting dilution. It was confirmed by restriction enzyme digestion and Southern blotting that the desired virus was obtained. These procedures will next be described in further detail.

(1) Construction of Shuttle Vector

Figure 2:
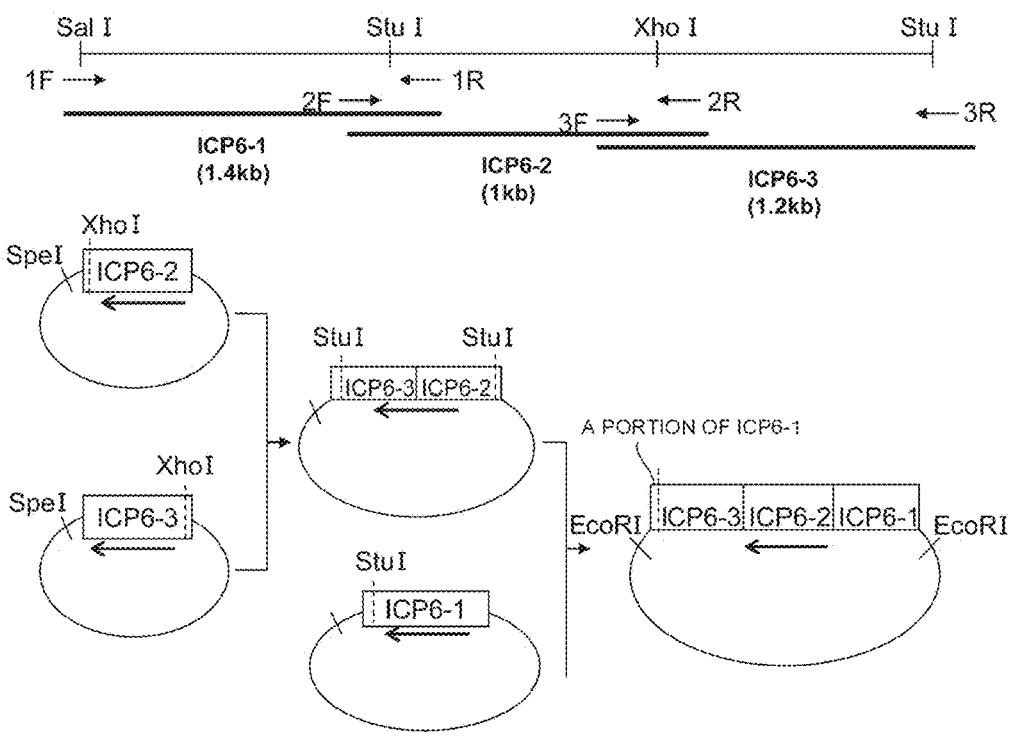
FIG. 2 is a conceptual diagram showing a step of producing a 3.4-kb ICP6 fragment by dividing the fragment into three fragments, amplifying them, and linking them to each other.

As shown in FIG. 2, the ICP6 gene fragment was divided into three fragments and they were amplified by PCR. The fragments thus obtained were inserted into a plasmid successively and linked to each other to obtain a 3.4-kb fragment. Primers used for amplifying these three fragments ICP6-1, ICP6-2, and ICP6-3 will be shown in Sequence Numbers: 1 to 6. The sequence of ICP6 was confirmed by ABI 377 DNA auto-sequencer (Applied Biosystems).

Next, a shuttle vector pVec-pro was prepared, which contained a 45-bp FRT adapter, a 50-bp loxP adapter, a lacZ gene derived from pcDNA6E/Uni-lacZ (Clontech), a 3.4-kb ICP6 gene, a 3,989-bp fragment of λHindIII, and a multicloning site with recognition sequences of restriction enzymes (ScaI, SpeI, SbfI, AflII, Acc65I, NheI, SwaI, and SalI).

The core promoter fragment (−367 to +56) of hTERT was PCR amplified from pGL3-378 (provided by Dr. Satoru Kyo/Kanazawa University) by using primers described in Sequence Nos: 7 and 8. After confirmation of the sequence of the hTERT promoter, it was inserted into the SpeI site of pVec-pro to obtain pVec-hTERT.

The osteocalcin (OC) promoter fragment was PCR amplified from an OC plasmid (OC-luc in PGL3 provided by Dr. Chinghai Kao/Indiana University; Matsubara S. et al., Cancer Res., 61:6012-6019, 2001) by using the primers described in Sequence Nos: 9 and 10. After confirmation of the sequence of the OC promoter, it was inserted into the SpeI/AflII site of pVec-pro to obtain pVec-OC.

The PSES promoter was obtained as a 467-bp AvrII/SmaI fragment from a plasmid containing a PSES promoter (PSES in GL3-Basic provided by Dr. Chinghai Kao/Indiana University; Lee S J et al., Mol Ther., 6:415-421, 2002). The PSES promoter was inserted into the SpeI/SwaI site of pVec-pro to obtain pVec-PSES.

The shuttle vector for constructing T-01 was constructed in a similar manner to the method of Fukuhara et al (Fukuhara et al, 2005) except that a transgene was not inserted.

(2) Insertion of Shuttle Vector to T-BAC Plasmid

A mixture of a T-BAC plasmid and each of the shuttle vectors obtained in (1) was incubated at 37° C. for 30 minutes in the presence of Cre recombinase (NEB) and electroporated into *E. coli* DH10B. The bacteria were streaked on an LB plate containing chloramphenicol (Cm; 15 μg/ml) and kanamycin (Kan; 10 μg/ml) and incubated overnight at 37° C. The integrity of DNA of each of the recombinant T-BAC plasmids was confirmed by endonuclease digestion and gel analysis.

(3) Transfection of Recombinant T-BAC Plasmid into Vero Cells—Purification of Virus Transfection of each of the recombinant T-BAC plasmids and pOG44 (Life Technologies) into Vero cells was conducted using Lipofectamine (Life Technologies) according to the written instructions. The transfected cells were incubated and the progeny virus was confirmed to be GFP negative through an inverted fluorescent microscope and also confirmed to be lacZ positive as a result of X-gal staining. Three rounds of limiting dilution analysis were conducted in order to obtain a single clone.

The recombinant virus was collected and the structure of the virus DNA was confirmed by HindIII digestion. The structure of the recombinant virus was confirmed also by Southern blotting. After HindIII digestion, the DNA fragment was isolated in a 0.6% (w/v) agarose gel in a 1×Trisborate-EDTA buffer by electrophoresis at 30V for 18 hours. The DNA probe of pcDNA6E/Uni-lacZ digested with EcoRI (corresponding to the sequence of lacZ) or the fragment of the PCR product of hTERT was labeled using an Alkphos Direct kit and CDP-Star detection (Amersham Bioscience).

(4) Confirmation of ICP6 Gene Expression

Expression of the ICP6 gene of each of the viruses was confirmed by Western blotting.

About $5\times10^5$ DU145 cells were infected with each of the viruses at MOI=0.02. Forty eight hours later, the resulting cells were washed with a RIPA buffer (150 mM NaCl, 1% NP-40, 0.5% DOC, 50 mM Tris-HCl, pH 8.0). Those cells in the buffer were placed on ice for 10 minutes, followed by centrifugal separation. The cell lysates (8 μg) were electrophoresed on a 10% SDS polyacrylamide gel and then transferred to Immobilon-P transfer membrane (Millipore) by using a semi-dry transfer blot system (Atto). After blocking for one hour with TBS containing 0.1% (v/v) Tween 20 and 5% (w/v) skim milk, the membrane and a primary antibody against Q3299 (1:250, corresponding to virus RR) were incubated for one hour, washed, and then incubated with an ECL-peroxidase-labeled anti-rabbit antibody (NA934VS; 1:10000) and HRP avidin. The protein was detected by ECL (enhanced chemiluminescence system; Fujifilm).

Figure 3:
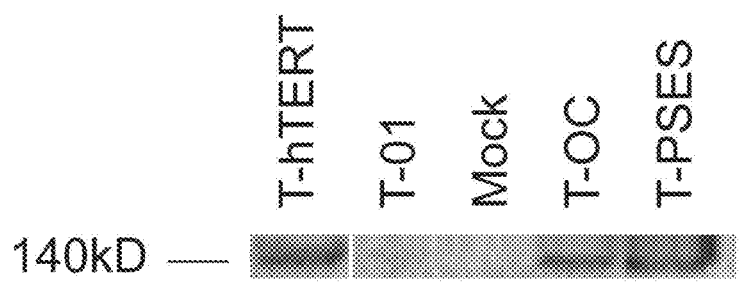
FIG. 3 shows the results of Western blotting conducted to confirm expression of RR in the recombinant herpes virus.

The results are shown in FIG. 3. A 140-kDA band corresponding to RR (ICP6 gene product) was observed from T-hTERT, T-PSES, and T-OC, while it was not observed from T-01.

Western blotting of T-hTERT and T-01 was also conducted using OSRC2 cells. Similarly, a 140 kDa-band was observed from T-hTERT, but it was not observed from T-01.

2. Investigation of Virus Replication Ability of Recombinant HSV-1

The replication ability of the recombinant HSV-1 thus constructed was measured in vitro. As cells, kidney cancer OSRC2 cells and DU145 prostate cancer cells, each having low RR activity and showing relatively slow growth, were used.

<Replication Ability in Kidney Cancer OSRC2 Cells>

Figure 4:
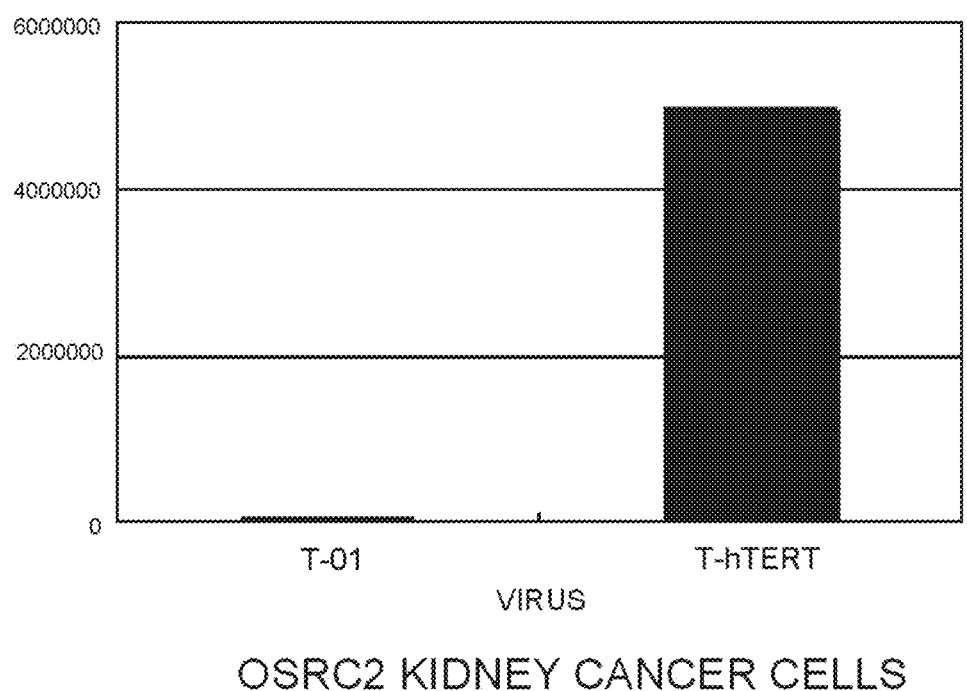
FIG. 4 shows the measurement results of growth ability of the recombinant Herpes virus in kidney cancer cells.

The kidney cancer OSRC2 cells were cultured on six-well plates at $5.0\times10^5$ cells/well. Twenty four hours later, the wells were infected with the viruses at multiplicities of infection (MOI) of 0.01 ($5.0\times10^3$ plaque-forming units (PFU)). At 48 hours post-infection, the viruses were collected. The cells were scraped and lysed by three cycles of freeze-thawing. The titer was measured according to the method of Todo et al (Proc Natl Acad Sci USA, 2001, 98:6396-6401). An average of the results of the test conducted twice is shown in FIG. 4.

With regards to the titer of the viruses thus collected, that of the T-01 virus was $2.2 \times 10^4$ pfu and that of the T-hTERT was $5.0 \times 10^6$ pfu, suggesting that the recombinant HSV-1 of the present invention has significantly increased virus replication ability in kidney cancer cells.

<DU145 Prostate Cancer Cells>

Figure 5:
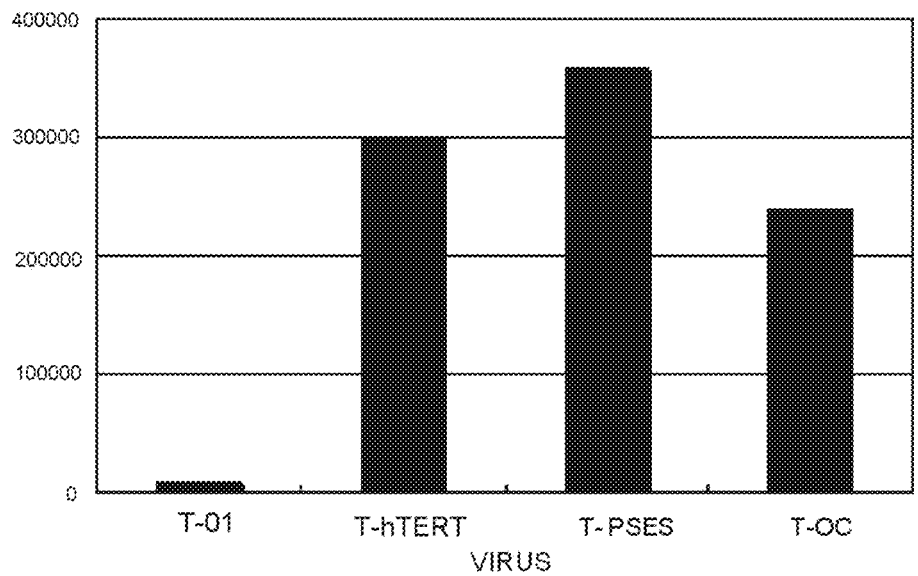
FIG. 5 shows the measurement results of growth ability of the recombinant herpes virus in prostate cancer cells.

DU145 prostate cancer cells were cultured on six-well plates at $5.0 \times 10^5$ cells/well. Twenty four hours later, the wells were infected with the viruses at multiplicities of infection (MOI) of 0.01 ($5.0 \times 10^3$ plaque-forming units (PFU)). At 48 hours post-infection, the viruses were collected and the titer was measured. An average of the results of the test conducted twice is shown in FIG. 5.

With regards to the titer of the viruses thus collected, those of the T-01, T-hTERT, T-PSES, and T-OC viruses were $7.8 \times 10^3$ pfu, $3.0 \times 10^5$ pfu, $3.6 \times 10^5$ pfu, $2.4 \times 10^5$ pfu, respectively, suggesting that the recombinant HSV-1 of the present invention has significantly increased virus replication ability in prostate cancer cells.

3. Investigation of Safety of Recombinant HSV-1

Safety test was conducted by stereotactically administering viruses to the brain of A/J mice sensitive to HSV-1.

Figure 6:
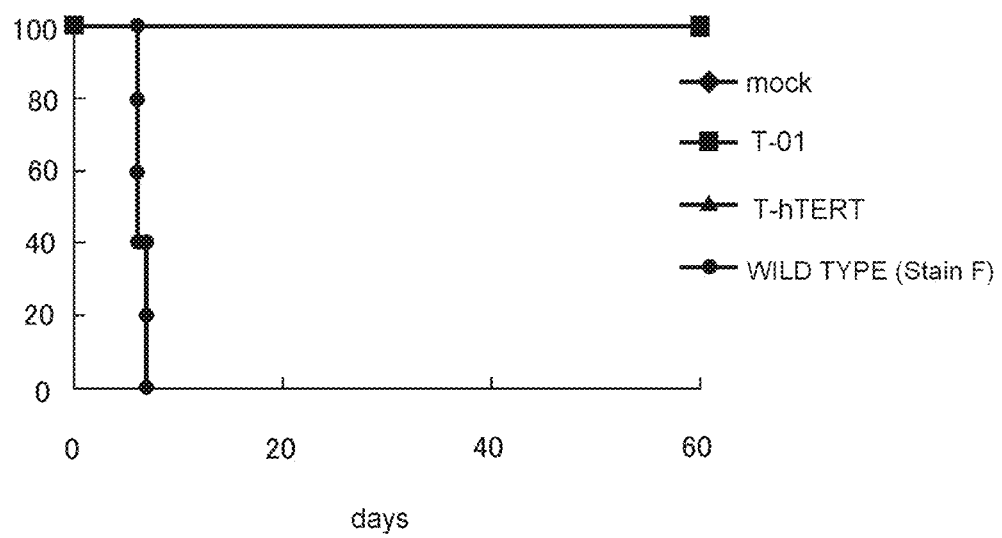
FIG. 6 shows the results of safety study conducted by intracerebral administration of the recombinant herpes virus and a wild type herpes virus to mice.

Five µl of each of the viruses, that is, $1.0 \times 10^6$ pfu T-01, $1.0 \times 10^6$ pfu T-hTERT, and $1.0 \times 10^3$ pfu wild type HSV-1 (strain F) was injected into to the right hemisphere of the brain of A/J mice (6-week old, female, n=5 per virus) over five minutes. A Kopf stereotactic frame (Kopf Instruments) was used. The clinical symptoms of the mice in a covered cage were monitored every day for three weeks. The results are shown in FIG. 6. The term "mock" as used in Examples after FIG. 6 means a mock-infected extract obtained by carrying out similar steps to those for the production of a virus stock except that Vero cells were not infected with the virus.

All the mice in the wild-type HSV-1 (strain F) administered group had died within 7 days of administration. Although in the T-hTERT administered group and T-01 administered group, viruses were administered in an amount 1000 times the amount of the strain F, all the mice survived and showed good health conditions during the entire follow-up period. It has been confirmed that T-hTERT has safety at least comparable to that of T-01.

4. Investigation of Antitumor Effects of Recombinant HSV-1 Against Kidney Cancer OSRC-2 Cells BALB/c nude mice were subcutaneously inoculated with $1 \times 10^7$ human kidney cancer OSRC-2 cells and a subcutaneous kidney cancer model was created according to the method of Fukuhara et al (Fukuhara et al, 2005).

Figure 7:
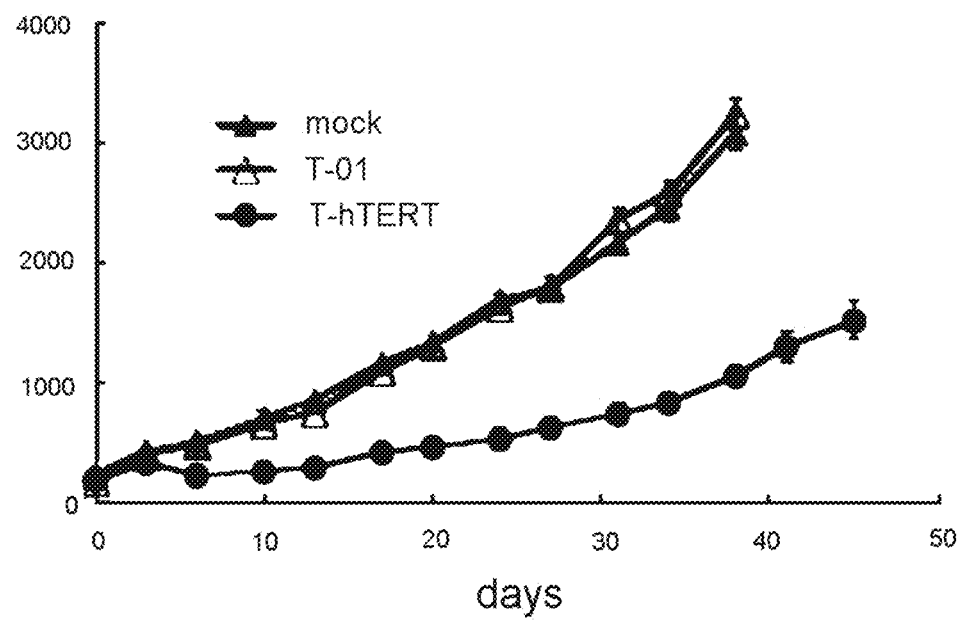
FIG. 7 shows the measurement results of antitumor effects of the recombinant Herpes virus administered to a subcutaneous kidney cancer model.

At the time when the subcutaneous tumor had a diameter of about 5 mm (Day 0 in the graph), the mock or $2 \times 10^5$ pfu T-01 or T-hTERT was administered into the tumor. Three days later (Day 3 in the graph), the same amount of viruses was administered again. The tumor tissue was measured and its volume was determined from length×width×height (mm). The results are shown in FIG. 7. The error bar in the graph shows the standard error of mean (SEM).

The T-hTERT administered group showed significantly high antitumor effects compared with the mock and T-01 administered groups (p<0.05 in t Test). The T-01 administered group did not show antitumor effects, presumably because due to low RR activity of kidney cancer OSRC-2 cells, deficiency of virus RR caused by deletion of ICP6 gene in the T-01 virus was not compensated.

Figure 8:
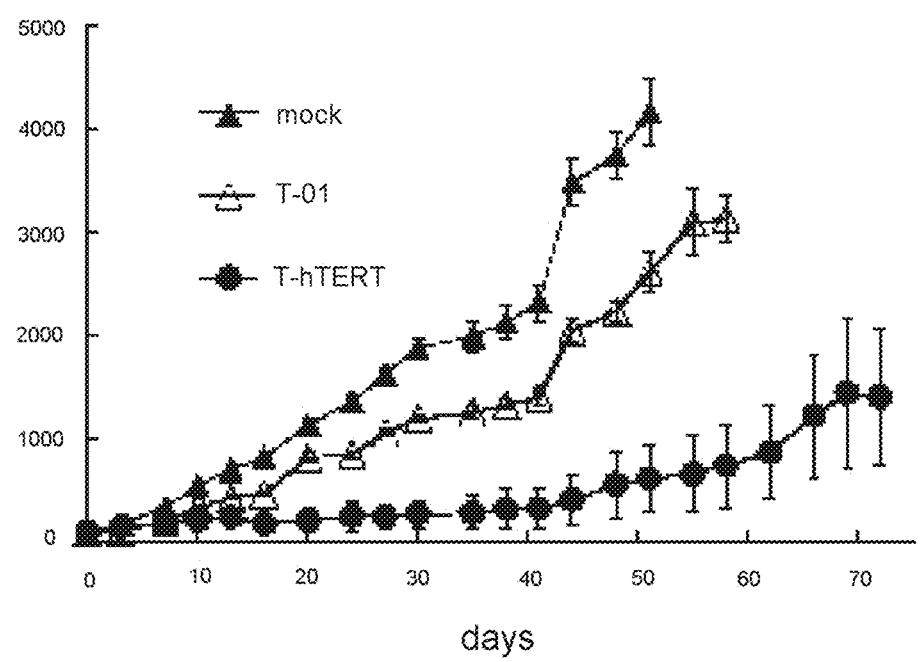
FIG. 8 shows the measurement results of antitumor effects of the recombinant herpes virus administered to a subcutaneous kidney cancer model (delayed administration model).

Next, when in a subcutaneous kidney cancer model similarly created, the tumor grew to 8 or 9 mm in diameter (Day 0 in the graph), the mock or $2 \times 10^5$ pfu T-01 or T-hTERT was administered into the tumor. Three days later (Day 3 in the graph), the same amount of the viruses was administered again. The results are shown in FIG. 8. The error bar in the graph shows the standard error of mean (SEM).

Even in a delayed administration model, in which administration is made after growth of tumors, T-hTERT showed significantly high antitumor effects compared with T-01 (p<0.05 in t Test). It has therefore been confirmed that T-hTERT is effective even after the tumor grows larger.

5. Investigation of Antitumor Effects of Recombinant HSV-1 Against Prostate Cancer DU145 Cells BALB/c nude mice were subcutaneously inoculated with $1 \times 10^7$ human prostate cancer DU145 cells and a subcutaneous prostate cancer model was created. It is known that the prostate cancer generally has low RR activity and grows slowly.

Figure 9:
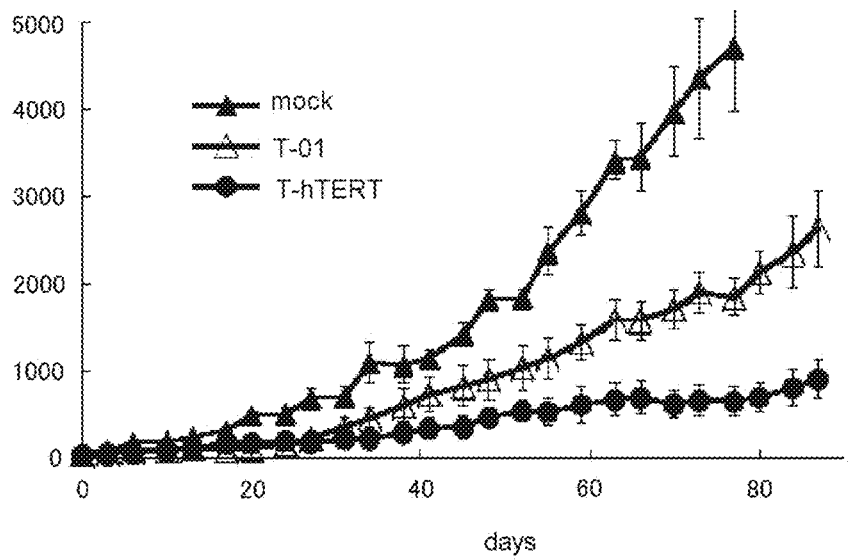
FIG. 9 shows the measurement results of antitumor effects of the recombinant herpes virus administered to a subcutaneous prostate cancer model.

At the time when the subcutaneous tumor grew to about 5 mm in diameter (Day 0 in the graph), the mock or $2 \times 10^5$ pfu T-01 or T-hTERT was administered into the tumor. Three days later (Day 3 in the graph), the same amount of the viruses was administered again. The tumor tissue was measured and its volume was determined from length×width×height (mm). The results are shown in FIG. 9. The error bar in the graph shows the standard error of mean (SEM).

Although T-01 had antitumor effects, T-hTERT showed significantly high antitumor effects compared with T-01 (p<0.05 in t Test).

6. Investigation of Antitumor Effect of Recombinant HSV-1 Against Malignant Brain Tumor U87MG Cells BALB/c nude mice were subcutaneously inoculated with $2 \times 10^6$ human malignant glioma U87MG cells and a subcutaneous malignant brain tumor model was created. It is known that the malignant brain tumor has high RR activity in tumor cells and grows quickly.

Figure 10:
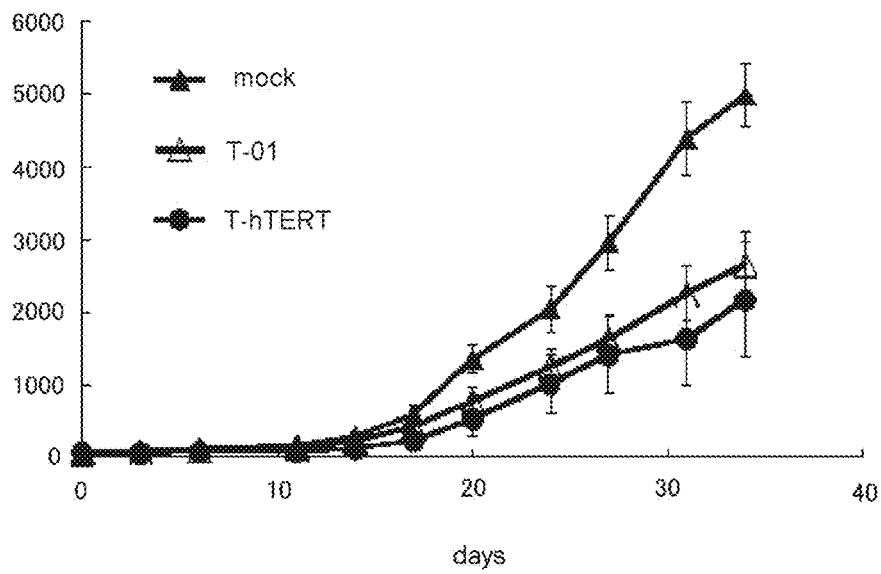
FIG. 10 shows the measurement results of antitumor effects of the recombinant herpes virus administered to a subcutaneous malignant brain tumor model.
Figure 11:
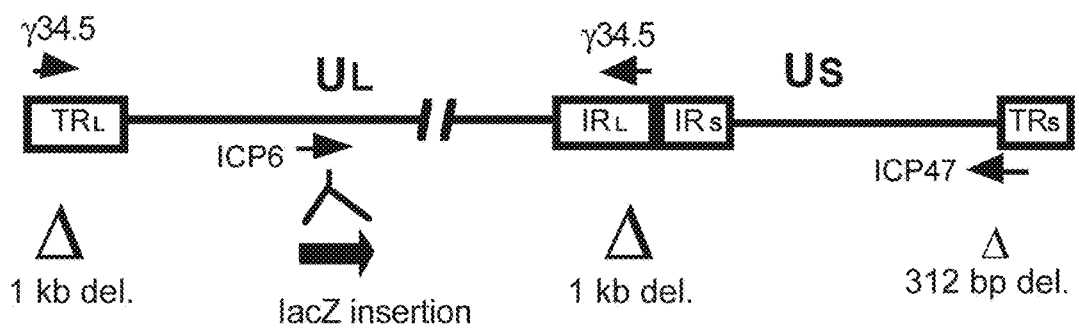
FIG. 11 is a schematic view showing the structure of G47Δ (a prior art)

At the time when the subcutaneous tumor grew to about 5 mm in diameter (Day 0 in the graph), the mock or $2 \times 10^5$ pfu T-01 or T-hTERT was administered into the tumor. Three days later (Day 3 in the graph), the same amount of the viruses was administered again. The tumor tissue was measured and its volume was determined from length×width×height (mm). The results are shown in FIG. 10. The error bar in the graph shows the standard error of mean (SEM).

Although T-hTERT showed significantly high antitumor effects compared with the control group (mock) (p<0.05 in t Test), there was no significant difference in antitumor effects against the malignant brain tumor having originally high RR activity between it and T-01.

Sequence Listing Free Text

Sequence No: 1 is a DNA sequence of a forward primer used for PCR amplification of an ICP6-1 fragment.

Sequence No: 2 is a DNA sequence of a reverse primer used for PCR amplification of an ICP6-1 fragment.

Sequence No: 3 is a DNA sequence of a forward primer used for PCR amplification of an ICP6-2 fragment.

Sequence No: 4 is a DNA sequence of a reverse primer used for PCR amplification of an ICP6-2 fragment.

Sequence No: 5 is a DNA sequence of a forward primer used for PCR amplification of an ICP6-3 fragment.

Sequence No: 6 is a DNA sequence of a reverse primer used for PCR amplification of an ICP6-3 fragment.

Sequence No: 7 is a DNA sequence of a forward primer used for PCR amplification of an hTERT core promoter fragment.

Sequence No: 8 is a DNA sequence of a reverse primer used for PCR amplification of an hTERT core promoter fragment.

Sequence No: 9 is a DNA sequence of a forward primer used for PCR amplification of an OC promoter fragment.

Sequence No: 10 is a DNA sequence of a reverse primer used for PCR amplification of an OC promoter fragment.

The invention claimed is:

1. A recombinant herpes simplex virus-1 comprising an endogenous large subunit of ribonucleotide reductase (ICP6) gene functionally linked to a tumor-specific promoter or a tissue-specific promoter, wherein the tumor-specific promoter or the tissue-specific promoter is heterologous to the ICP6 gene.

2. The recombinant herpes simplex virus-1 according to claim 1, wherein the tumor-specific promoter or the tissue-specific promoter is a promoter selected from the group consisting of a human telomerase reverse transcriptase (hTERT) promoter, a prostate-specific enhancer sequence (PSES) promoter, and an osteocalcin (OC) promoter.

3. The recombinant herpes simplex virus-1 according to claim 1, wherein a γ34.5 gene and/or an ICP47 gene is deleted or inactivated.

4. The recombinant herpes simplex virus-1 according to claim 3, wherein the γ34.5 gene is deleted or inactivated.

5. The recombinant herpes simplex virus-1 according to claim 3, wherein the ICP47 gene is deleted or inactivated.

6. The recombinant herpes simplex virus-1 according to claim 3, wherein the γ34.5 gene is deleted or inactivated and the ICP47 gene is deleted or inactivated.

7. A pharmaceutical composition comprising the recombinant herpes simplex virus-1 as claimed in claim 1 as an active ingredient.

8. The pharmaceutical composition according to claim 7, which is a therapeutic agent for a tumor.

9. The pharmaceutical composition according to claim 8, wherein the tumor is selected from the group consisting of tumors with a low growth rate, benign tumors, and tumors with low ribonucleotide reductase activity.

10. The pharmaceutical composition according to claim 8, wherein the tumor is selected from the group consisting of prostate cancer, kidney cancer, breast cancer, chondrosarcoma, and meningioma.

11. A method of treating a tumor in a subject, comprising administering a therapeutically effective amount of the recombinant herpes simplex virus-1 as claimed in claim 1 directly to the tumor in the subject.

12. The recombinant herpes simplex virus-1 according to claim 1, wherein the endogenous ICP6 gene is functionally linked to the tissue-specific promoter.

13. The recombinant herpes simplex virus-1 according to claim 1, wherein the recombinant herpes simplex virus-1 exhibits high replication ability in tumor cells having low ribonucleotide reductase (RR) activity as compared to an HSV construct having a deleted or inactivated ICP6 gene.

14. The recombinant herpes simplex virus-1 according to claim 13, wherein the HSV construct is T-01 or G474.

15. The recombinant herpes simplex virus-1 according to claim 13, wherein the tumor cells having a low ribonucleotide reductase (RR) activity are kidney cancer OSRC2 cells or DU145 prostate cancer cells.

16. An oncolytic therapeutic comprising a recombinant herpes simplex virus-1 having an endogenous large subunit of ribonucleotide reductase (ICP6) gene functionally linked to a tumor-specific promoter or a tissue-specific promoter, wherein the tumor-specific promoter or the tissue-specific promoter is heterologous to the ICP6 gene, and one or both the γ34.5 genes being inactivated or deleted.

* * * * *